(12) United States Patent
May et al.

(10) Patent No.: US 9,289,752 B2
(45) Date of Patent: Mar. 22, 2016

(54) CATALYST FOR REACTING CARBOXYLIC ACID NITRILES

(75) Inventors: Alexander May, Seeheim-Jugenheim (DE); Bernd Vogel, Wiesbaden (DE); Hermann Siegert, Seeheim-Jugenheim (DE); Kurt-Alfred Gaudschun, Oer-Erkenschwick (DE); Thomas Quandt, Marl (DE)

(73) Assignee: Evonik Röhm GmbH, Darmstadt (DE)

( * ) Notice: Subject to any disclaimer, the term of this patent is extended or adjusted under 35 U.S.C. 154(b) by 465 days.

(21) Appl. No.: 12/937,659

(22) PCT Filed: Feb. 26, 2009

(86) PCT No.: PCT/EP2009/052239
§ 371 (c)(1),
(2), (4) Date: Oct. 13, 2010

(87) PCT Pub. No.: WO2009/130075
PCT Pub. Date: Oct. 29, 2009

(65) Prior Publication Data
US 2011/0034728 A1 Feb. 10, 2011

(30) Foreign Application Priority Data
Apr. 22, 2008 (DE) .................. 10 2008 001 319

(51) Int. Cl.
| | | |
|---|---|---|
| *B01J 21/08* | (2006.01) | |
| *B01J 23/34* | (2006.01) | |
| *B01J 37/00* | (2006.01) | |
| *C07C 231/06* | (2006.01) | |
| *B01J 35/00* | (2006.01) | |

(52) U.S. Cl.
CPC .............. *B01J 23/34* (2013.01); *B01J 37/0009* (2013.01); *B01J 37/0063* (2013.01); *C07C 231/065* (2013.01); *B01J 35/002* (2013.01)

(58) Field of Classification Search
None
See application file for complete search history.

(56) References Cited

U.S. PATENT DOCUMENTS

| | | | |
|---|---|---|---|
| 3,366,639 A | | 1/1968 | Haefele et al. |
| 4,290,923 A | | 9/1981 | Mein et al. |
| 5,232,886 A | | 8/1993 | Yoshimoto et al. |
| 5,653,949 A | | 8/1997 | Chen et al. |
| 5,721,037 A | | 2/1998 | Kumazawa et al. |
| 6,146,451 A | * | 11/2000 | Sakata et al. ............. 96/135 |
| 2007/0117980 A1 | | 5/2007 | Weigel et al. |
| 2008/0194862 A1 | | 8/2008 | Ackermann et al. |
| 2009/0182167 A1 | | 7/2009 | May et al. |
| 2010/0029979 A1 | | 2/2010 | Vogel et al. |
| 2011/0060159 A1 | | 3/2011 | May et al. |
| 2011/0306784 A1 | | 12/2011 | May et al. |

FOREIGN PATENT DOCUMENTS

| | | |
|---|---|---|
| DE | 2 131 813 | 3/1972 |
| DE | 10 2006 055 430 A1 | 5/2008 |
| EP | 0 379 111 A2 | 7/1990 |
| EP | 1300192 * | 4/1996 |
| EP | 0956898 * | 4/1999 |
| EP | 0 945 429 A1 | 9/1999 |
| EP | 0 956 898 | 11/1999 |
| EP | 1 300 192 | 4/2003 |
| JP | 61-64334 A | 4/1986 |
| JP | 6-340602 A | 12/1994 |
| JP | 9-104665 | 4/1997 |
| JP | 11-319558 A | 11/1999 |
| WO | 2007 039536 | 4/2007 |
| WO | 2008 061822 | 5/2008 |

OTHER PUBLICATIONS

Search Report issued Apr. 15, 2009 in German Patent Application No. 10 2008 001 319.6 (with English translation of Category of Cited Documents).
Office Action issued Oct. 18, 2012 in Egyptian Patent Application No. 1752/2010.
International Search Report issued Nov. 23, 2009 in PCT/EP09/52239 filed Feb. 26, 2009.
Combined Chinese Office Action and Search Report issued Aug. 3, 2012 in Chinese Patent Application No. 200980114165.9 (English-language translation only).
Communication pursuant to Article 94(3) EPC issued Sep. 8, 2014 in European Patent Application No. 09 734 323.0 (with English language translation).
Ferdi Schüth, et al., "Catalyst Forming" Handbook of Heterogeneous Catalysis 2$^{nd}$ Edition, XP055136695, Feb. 2008, pp. 676-699 and cover page.
"Structure and Composition of Clay Minerals" Ullmann's Encyclopedia of Industrial Chemistry 5$^{th}$ edition, vol. A7, XP055136697, 1986, 6 pages.
Office Action issued Mar. 13, 2013, in Japanese Patent Application No. 2011-505440 submitting German translation only.

* cited by examiner

*Primary Examiner* — Melvin C Mayes
*Assistant Examiner* — Colette Nguyen
(74) *Attorney, Agent, or Firm* — Oblon, McClelland, Maier & Neustadt, L.L.P

(57) ABSTRACT

The present invention relates to a catalyst for reacting carbonitriles with water, wherein the catalyst comprises at least 60% by weight of manganese dioxide with an empirical formula MnOx where x is in the range from 1.7 to 2.0, and at least one plasticizer. The present invention further relates to a process for preparing the catalysts detailed above and to a process for preparing carboxamides by reacting carbonitriles with water in the presence of the present catalyst.

24 Claims, No Drawings

CATALYST FOR REACTING CARBOXYLIC ACID NITRILES

The present invention relates to a catalyst for preparing carboxamides by reacting carbonitriles with water. The present invention further relates to a process for preparing these catalysts.

The preparation of carboxamides by the reaction of carbonitriles with water in the presence of a catalyst comprising manganese dioxide has been prior art for some time. Carboxamides are frequently required as intermediates in industry. For example, $\alpha$-hydroxyiso-butyramide may serve to prepare methacrylic acid or methacrylic esters, especially methyl methacrylate.

As an illustrative example of many documents, reference is made to the publication DE 1593320. DE 1593320 describes a process for hydrolysing nitriles to amides with the aid of manganese dioxide, in which yields up to more than 90% have been achieved with aliphatic nitriles. This process affords good yields coupled with a high rate. However, disadvantages are the low service life and the mechanical stability of the catalyst. In continuous processes, production therefore has to be stopped after a short time to exchange the catalyst. This operation is associated with very high costs, the productivity of the overall process being lowered by the stoppage.

The patent JP 09104665 describes the preparation of active $\delta$-manganese dioxide and defines its activity via the size of the surface area. The catalyst described herein exhibits a very high activity.

However, the above-described problem of low service life exists here too. This is especially true of catalysts which have a particularly high surface area.

To improve the lifetime of the catalysts used for hydrolysis, many efforts have already been made. For example, the document EP 379 111 A2 describes the hydrolysis of $\alpha$-hydroxycarbonitriles in the presence of manganese dioxide catalysts which have a high content of alkali metals. By virtue of this high content of alkali metals, these catalysts exhibit a particularly high activity and service life. The hydrolysis can be carried out especially at a pH in the range from 4 to 8. However, a pH within this range without the use of the catalysts specified in detail in this publication does not lead to a long service life of the catalysts (cf. EP 379 111 A2 comparative example 1). Furthermore, this catalyst does not satisfy the mechanical demands which are made on these catalysts in many plants.

In addition, the publication EP 545 697 A1 describes the use of particular heteropolyacids in order to improve the lifetime of the catalyst. A further improvement in the service life of the catalyst can be achieved by the use of promoters. The compounds are added to the system during the reaction. The pH in the hydrolysis reaction should be less than 4, since the acetone cyanohydrin used otherwise lowers the lifetime of the catalyst. At pH values above 4, the acetone cyanohydrin used can decompose readily, which can form by-products which impair the catalyst properties. This publication explicitly contradicts the teaching of the document EP 379 111 A2 (cf. EP 545 697 A1, page 3 lines 3 to 6).

In addition, the publication EP 433 611 A1 describes the use of oxidizing agents to stabilize the catalysts. Similarly, the document EP 945 429 A1 describes the use of oxidizing agents to prolong the catalyst service life, a further improvement being achievable by the addition of small amounts of amines. An adjustment of the pH to a predefined value is not described in either of documents EP 433 611 A1 and EP 945 429 A1, an improvement in the service life of catalysts being achievable solely through the use of amines according to document EP 773 212 A1. The improvement described in EP 945 429 A1 therefore does not result from an adjustment of the pH, but rather from the combination of the teachings of documents EP 773 212 A1 and EP 433 611 A1. In this context, it should be emphasized that especially cyanohydrins are generally stabilized by addition of acids, and so the test data disclosed in the examples have probably been obtained under acidic conditions. This is also evident, for example, from the publication EP 379 111 A2 cited above. It is therefore impossible to conclude a particular pH from the tests disclosed in documents EP 433 611 A1 and EP 945 429 A1.

In addition, catalysts comprising manganese dioxide for the preparation of carboxamides are disclosed in publication EP 0 956 898 A2. According to this publication, the mechanical stability of the catalysts can be improved by the use of $SiO_2$. In this case, the binder can be added as early as during the precipitation of the $MnO_2$. However, it is found that the catalysts thus obtained have a profile of properties which does not satisfy particularly high demands.

For some reactor systems, the catalysts must have a particular shape. EP 0 956 898 A2 states that the materials used to prepare the catalyst can be extruded. However, when these tests are reworked, the apparatus used for shaping is subjected to an extremely high level of stress, which can lead to premature failure of this apparatus.

Even though the teachings of the documents cited above already lead to an improvement in the catalyst properties, there is a permanent need to improve the mechanical stability, especially the abrasion resistance and the pressure stability, coupled with very high activity of the catalyst. A further need of development exists with regard to improving the lifetime, in order to prolong the exchange cycles in the case of continuous operation of the plants, and to reduce the costs of the exchange of the catalyst. In this connection, it should be specified that very large amounts of catalyst are required.

In view of the prior art, it is thus an object of the present invention to provide a catalyst for reacting carbonitriles with water, which has an excellent activity coupled with high mechanical stability. In particular, the catalyst should exhibit a high pressure stability and a high abrasion resistance. Furthermore, the catalyst should lead to a particularly high selectivity and a high conversion of the catalysed reaction. Moreover, the catalyst or the material used to produce the catalyst should be shapeable in a simple and inexpensive manner. At the same time, the apparatus used for the shaping should be subjected to a relatively low level of stress, such that premature failure of the apparatus can be avoided.

A further object of the present invention can be considered that of providing a process for preparing carboxamides, which can be carried out particularly simply and inexpensively and with a high yield. A particular problem was more particularly to provide a process which, at a high rate, low energy input and low yield losses, ensures a particularly long service life of the catalyst.

These objects and further objects which are not stated explicitly but which are immediately derivable or discernible from the connections discussed herein by way of introduction are achieved by virtue of a catalyst having all features of claim 1. Appropriate modifications to the inventive catalysts are protected in subclaims. A process for preparing the catalysts detailed above is the subject of claim 13. With regard to the process for preparing carboxamides, claim 21 provides a solution to the problem underlying this object.

The present invention accordingly provides a catalyst for reacting carbonitriles with water, which is characterized in that the catalyst comprises at least 60% by weight of manganese dioxide with an empirical formula $MnO_x$ where x is in the range from 1.7 to 2.0, and at least one plasticizer.

These measures surprisingly make it possible to provide a catalyst for reacting carbonitriles with water, which exhibits a particularly excellent profile of properties. For instance, a catalyst of the present invention has an excellent activity coupled with high mechanical stability. At the same time, the inventive catalyst leads to a surprisingly high selectivity of the reaction, which can be carried out at a high conversion without an increased degree of side reactions occurring. Furthermore, the catalyst exhibits a high pressure stability and a high abrasion resistance. In addition, the catalyst can be shaped simply and inexpensively. At the same time, the apparatus used for the shaping is subjected to a relatively low level of stress, such that premature failure of the apparatus can be avoided.

Furthermore, a catalyst of the present invention enables a surprisingly advantageous process for preparing carboxamides by reacting carbonitriles with water. This reaction is also referred to hereinafter as hydrolysis. One of the surprising advantages is that the process according to the invention, at a high rate, low energy input and low yield losses, ensures a particularly long service life of the catalyst. This allows the process to be carried out particularly efficiently and inexpensively, since an operational stoppage to exchange the catalyst is needed only rarely in the course of continuous operation of the plant.

The catalyst of the present invention comprises at least 60% by weight, preferably at least 80% by weight, of manganese dioxide with an empirical formula $MnO_x$ where x is in the range from 1.7 to 2.0. Manganese dioxide exists in several polymorphs. They differ significantly in their behaviour as a catalyst. Pyrolysite (beta-manganese dioxide), the most stable polymorph, has the most marked crystallinity. The crystallinity is less marked in the further modifications and extends down to amorphous products, which include α- or δ-$MnO_2$. The polymorphs can be assigned by X-ray diffraction. The chemically and catalytically particularly active forms of manganese dioxide may be partly hydrated and additionally contain hydroxyl groups.

The manganese dioxide-comprising catalyst may comprise further compounds or ions. These include especially alkali metal and/or alkaline earth metal ions, which can be introduced into the crystal lattice of the $MnO_2$ or deposited on the surface of the $MnO_2$ or another component of the catalyst in the course of preparation. The preferred alkali metal ions include especially lithium, sodium and/or potassium ions. The preferred alkaline earth metal ions include especially calcium and/or magnesium ions. The content of alkali metal and/or alkaline earth metal may preferably be less than 0.6 atom per atom of manganese. The atomic ratio of alkali metal and/or alkaline earth metal to manganese is preferably in the range from 0.01:1 to 0.5:1, more preferably in the range from 0.05:1 to 0.4:1.

In addition, the manganese dioxide-comprising catalyst may comprise promoters, which can likewise be introduced into the crystal lattice of the $MnO_2$ or deposited on the surface of the $MnO_2$ or of another component of the catalyst. The preferred promoters include Ti, Zr, V, Nb, Ta, Cr, Mo, W, Zn, Ga, In, Ge, Sn and Pt. The content of promoters may preferably be less than 0.3 atom per atom of manganese. The atomic ratio of promoter to manganese is preferably in the range from 0.001:1 to 0.2:1, more preferably in the range from 0.005:1 to 0.1:1. The manganese dioxide-comprising catalyst may preferably comprise 0.01 to 10% by weight, more preferably 0.1 to 5% by weight, of promoters, this parameter being based on the weight measured as the metal or metal ion.

Preferred manganese dioxide has, in the X-ray spectrum (XRD), measured as a powder, at least one reflection in the range from 32.0 to 42.0°. The X-ray spectra can be obtained, for example, with an Xpert pro instrument from Panalytical. This reflection in the range from 32.0 to 42.0° more preferably has the highest intensity in relation to the further intensities in the range from 20° to 65°, measured as the maximum of the reflection. Particularly preferred manganese dioxide for preparing the catalysts exhibits a low crystallinity, which can be seen, inter alia, from the X-ray spectrum. The structure of particularly preferred manganese dioxide can be assigned to the structure number 44-0141 or 72-1982, which is described in ICDD (International Centre for Diffraction Data), particular preference being given to manganese dioxide with a structure according to 44-0141.

The alkali metal and/or alkaline earth metal ions and the promoters can be added, for example, in the form of salts in the course of preparation of the manganese dioxide or of the catalyst. For instance, it is possible to use especially halides, nitrates, sulphates, carbonates, phosphates and hydroxides of the aforementioned substances, preference being given to using compounds which are soluble in water.

In a particular aspect of the present invention, the manganese dioxide used to prepare an inventive catalyst may have a specific surface area (BET) in the range from 50 to 1000 $m^2$ per g, more preferably 100 to 300 $m^2$ per g and most preferably 150 to 250 $m^2$ per g, which is determined by the test method DIN 66131.

The preparation of manganese dioxide which can be used for the preparation of inventive catalysts is known per se and is described, for example, in EP-A-0 379 111, EP-A-0 956 898, EP-A-0545697 and EP-A-0 433 611. The manganese dioxides for use in accordance with the invention can preferably be obtained by oxidation of $Mn^{2+}$ salts, for example $MnSO_4$, with permanganates, for example potassium permanganate (cf. Biochem. J., 50, p. 43 (1951) and J. Chem. Soc., p. 2189, 1953). In addition, suitable manganese dioxide can be obtained by electrolytic oxidation of manganese sulphate in aqueous solution.

Manganese dioxide which can be used in accordance with the invention to prepare catalysts, with structures according to 44-0141, can be obtained, for example, by adding an aqueous solution containing 0.71 mol of Mn(II) $SO_4$ (total of 15% by weight of $Mn^{2+}$ in solution), 0.043 mol of $Zr(IV)(SO_4)_2$, 0.488 mol of conc. sulphuric acid and 13.24 mol of water at 70° C. rapidly to a solution of 1.09 mol of $KMnO_4$ in 64.5 mol of water. The supernatant solution with the precipitate formed can be heated to 90° C. for 3 hours. The precipitate can subsequently be filtered off, washed four times with one liter of water and dried at 110° C. for 12 hours.

In addition to the manganese dioxide described above, which may optionally be provided with promoters or further additives, an inventive catalyst comprises at least one plasticizer.

The plasticizer enables simple and stable shaping of the inventive catalyst. The plasticizer is accordingly a compound which improves the plastic deformability of a material for producing the catalyst. This improves the property of a material for preparing the inventive catalyst of becoming shapeable (of flowing) after addition of a particular amount of liquid (usually water) and under a particular pressure without breaking, the new form being retained after the shaping has ended (after decompression). This property is achieved, for example, in the case of sliding of the particles present in a material for preparing the catalyst over one another. In order to maintain the shape, the pressure applied is initially opposed by a resistance (the substance behaves elastically). When the pressure reaches a particular minimum, the yield value, the material begins to flow. This type of flow is then referred to as elastically plastic flow, for delimitation from viscous flow in the case of liquids. It is surprisingly possible, through the use of plasticizers, especially in the case of addition of binders or in the case of use of plasticizers which serve as binders, to improve the mechanical properties, for example the abrasion resistance and the compressive strength, of the catalyst. At the same time, it is surprisingly possible to maintain the high activity and lifetime of the catalyst at a high level or to improve it.

The plasticizers used may be organic compounds which can preferably be essentially removed from the catalyst at low temperatures of below 400° C., preferably below 250° C.

Preferred plasticizers comprise silicon dioxide ($SiO_2$). The plasticizer is preferably a clay mineral, especially a sheet silicate, for example dickite, flint, illite, nontronite, hectorite, kaolinite, montmorillonite. Preferred silicon dioxide-comprising plasticizers have a marked platelet structure and a high fineness. The particle size is preferably less than 1500 nm, preferably less than 700 nm, measured as the D95 value, which can be determined, for example, by means of sedimentation. For this purpose, it is possible to use, inter alia, the SediGraph© 5100 instrument from Micromeritics GmbH. The use of silicon dioxide-containing plasticizers allows the mechanical properties of the catalyst detailed above to be improved unexpectedly.

Preferred plasticizers have a Moh's hardness in the range from 0.5 to 3, more preferably in the range from 1.5 to 2.

Appropriately, an inventive catalyst generally comprises 0.1 to 30% by weight, more preferably 1 to 15% by weight, of plasticizers, without any intention that this should impose a restriction.

The catalyst preferably comprises at least one binder. In this case, the plasticizer itself may serve as a binder. In addition, it is possible to add compounds which do not have any plasticizing action as binders. The binder brings about mechanical stability and compressive strength of the catalyst which satisfies many requirements. The binder preferably comprises silicon dioxide ($SiO_2$), particular preference being given especially to silicates with a specific surface area in the range from 50 to 1200 $m^2/g$, more preferably in the range from 150 to 400 $m^2/g$. In a particular aspect of the present invention, the binder may comprise various compounds each of which comprise $SiO_2$. The binder more preferably comprises a silicate which is pulverulent in the course of preparation of the catalyst, it being particularly preferable to use framework silicates and/or precipitated silicas. Pulverulent binders preferably have a particle size in the range from 0.2 to 200 μm, more preferably in the range from 2 to 50 μm, measured by means of laser diffraction, for example a Malvern Mastersizer® type 2000.

In addition, it is possible to use an $SiO_2$ as the binder, which is present in the form of a silica sol in the course of preparation of the catalyst. A silica sol for use with preference to prepare the present catalyst preferably has a particle size in the range from 1 to 100 nm, more preferably 5 nm to 75 nm and most preferably in the range from 7 to 10 nm, based on the diameter of the particles.

Particular configurations of inventive catalysts preferably comprise a binder which is present in the form of a silica sol in the course of preparation of the catalyst, and a binder which is pulverulent in the course of preparation of the catalyst. Appropriately, the weight ratio of silica sol to pulverulent binder may be in the range from 20:1 to 1:1, more preferably 15:1 to 5:1, these data being based on the solids content of the silica sol.

The proportion of binder in the catalyst is preferably in the range from 0.9% by weight to 30% by weight, more preferably in the range from 2% by weight to 20% by weight.

Appropriately, the total amount of plasticizer and binder may be in the range from 1 to 30% by weight, more preferably in the range from 3 to 20% by weight, based on the weight of the catalyst. The weight ratio of binder to plasticizer is preferably in the range from 200:1 to 1:20, more preferably 20:1 to 5:1. These data are based especially on binders which have only a low plasticizing effect, if any. Binders which have a plasticizing effect are assigned in this context to the plasticizers. In the case of use of binders or plasticizers which comprise liquids in the course of preparation of the catalyst, these data are based on the solids content of the binder or plasticizer.

Particularly preferred catalysts comprise, for example,
1.0 to 30% by weight, especially 3 to 20% by weight, of $SiO_2$;
0.1 to 10% by weight, especially 2 to 7% by weight, of $K_2O$;
0.0 to 5% by weight, especially 0.2 to 4% by weight, of $ZrO_2$ and
75 to 99% by weight, especially 85 to 98% by weight, of $MnO_2$. The catalyst may comprise further elements as has been described above. The composition of the catalysts can be determined by semiquantitative X-ray fluorescence analysis.

The catalyst can preferably be used, for example, in the form of granule or of dried agglomerates, and the particle size may in many cases be dependent on the reaction vessel used. Preferred dried agglomerates exhibit a diameter in the range from 0.5 to 5 mm, more preferably 1 to 3 mm. Appropriate diameters of preferred extrudates are in the range from 0.4 mm to 10 mm, more preferably in the range from 0.8 mm to 6 mm. The length of preferred extrudates is in the range from 2 mm to 10 mm, more preferably in the range from 3 mm to 5 mm.

The inventive catalyst can preferably be prepared by a process in which at least one pulverulent manganese dioxide and at least one pulverulent plasticizer are mixed to obtain agglomerates.

The mixture comprising at least one pulverulent manganese dioxide and at least one pulverulent plasticizer can preferably be admixed with a liquid binder in order to obtain agglomerates.

A liquid binder is understood herein to mean a composition which is present in free-flowing form and is capable, if appropriate after drying, of binding the components of the catalyst, i.e. of improving the mechanical properties such as the compressive strength and the abrasion resistance. The liquid binder preferably comprises water, more preferably at least one silica sol.

Appropriately, the agglomerates detailed above can be obtained by the use of an intensive mixer. Intensive mixers are apparatus which can bring about a high energy input into a system. Intensive mixers are known per se. These include, for example, Eirich mixers and Z-arm kneaders. In this context, the agglomeration behaviour can be influenced via the binder content, the moisture content, the product fineness and the energy input, especially the mixer speed and geometry, the fill level and the run time. Valuable information on this subject can be found especially in the examples adduced.

The processing of the composition in the intensive mixer achieves intensive mixing of all components and precompaction of the material. The precompaction is achieved by introduction of energy through the motions of the internals present in the intensive mixer, which may include, for example, an agitator and a wiper, and the associated shear forces.

The agglomerates thus prepared may either be used directly as a catalyst after drying in the form of "pellets" or else be subjected to further shaping in various ways in the moist state. The size of the dried agglomerates is preferably in the range from 0.5 to 5 mm, more preferably 1 to 3 mm, these figures being based especially on spherical agglomerates.

In a particular aspect of the present invention, the agglomerates initially obtained can be extruded. It is surprisingly possible to extrude mixtures to prepare an inventive catalyst in a particularly simple manner.

These mixtures can be converted, for example, by simple drying to a high-activity catalyst. Surprisingly, extrusion can improve the selectivity and the activity of the catalysts, the enhanced activity being manifested, for example, by an improved conversion.

Shaping is possible, for example, using the following machines

Händle screw extruder (PZVM8b type)
Hutt granule shaping machine system (GR 1 type)
Schlüter annular die press (PP 127 type)
Sproud Waldron annular die press In addition to a circular cross section, special shapes such as "trilobe" (=cloverleaf shape) or rings are also possible.

The moist aggregates or the extrudates are preferably dried at a temperatures which does not lead to any significant impairment in the catalytic activity of the catalysts. The drying temperature is preferably in the range from 10 to 200° C., more preferably in the range from 80 to 120° C. The drying time may, depending on the drying temperature and the pressure at which the drying takes place, be within a wide range. In many cases, a sufficient drying time is in the range from 10 minutes to 30 hours, more preferably in the range from 20 minutes to 10 hours.

The catalyst of the present invention has outstanding mechanical properties.

The inventive catalyst enables the efficient preparation of carboxamides. The carbonitriles used here are especially those which generally have groups of the formula —CN. Carboxamides comprise at least one group of the formula —CONH$_2$. These compounds are known in the technical field and are described, for example, in Römpp Chemie Lexikon 2nd edition on CD-ROM.

The reactants used may especially be aliphatic or cycloaliphatic carbonitriles, saturated or unsaturated carbonitriles and aromatic and heterocyclic carbonitriles. The carbonitriles for use as reactants may have one, two or more nitrile groups. In addition, it is also possible to use carbonitriles which have heteroatoms, especially halogen atoms, such as chlorine, bromine, fluorine, oxygen, sulphur and/or nitrogen atoms, in the aromatic or aliphatic radical. Particularly suitable carbonitriles preferably comprise 2 to 100, preferably 3 to 20 and most preferably 3 to 5 carbon atoms.

The aliphatic carbonitriles which each have a saturated or unsaturated hydrocarbon group include acetonitrile, propionitrile, butyronitrile, isobutyronitrile, valeronitrile, isovaleronitrile, capronitrile and other saturated mononitriles; malonitrile, succinonitrile, glutaronitrile, adiponitrile and other saturated dinitriles; α-aminopropionitrile, α-aminomethylthio-butyronitrile, α-aminobutyronitrile, aminoacetonitrile and other α-aminonitriles; cyanoacetic acid and other nitriles each with a carboxyl group; amino-3-propionitrile and other β-aminonitriles; acrylonitrile, methacrylonitrile, allyl cyanide, crotononitrile or other unsaturated nitriles, and cyclopentane carbonitrile and cyclohexane carbonitrile or other alicyclic nitriles.

The aromatic carbonitriles include benzonitrile, o-, m- and p-chlorobenzonitrile, o-, m- and p-fluorobenzonitrile, o-, m- and p-nitrobenzonitrile, p-aminobenzonitrile, 4-cyanophenol, o-, m- and p-tolunitrile, 2,4-dichlorobenzonitrile, 2,6-dichlorobenzonitrile, 2,6-difluorobenzonitrile, anisonitrile, α-naphthonitrile, β-naphthonitrile and other aromatic mononitriles; phthalonitrile, isophthalonitrile, terephthalonitrile and other aromatic dinitriles; benzyl cyanide, cinnamoylnitrile, phenylacetonitrile, mandelonitrile, p-hydroxyphenylacetonitrile, p-hydroxyphenylpropionitrile, p-methoxyphenylacetonitrile and other nitriles which each have an aralkyl group.

The heterocyclic carbonitriles include especially nitrile compounds which each have a heterocyclic group which contains a 5- or 6-membered ring and has at least one atom which is selected from the group consisting of a nitrogen atom, an oxygen atom and a sulphur atom as a heteroatom, for example 2-thiophenecarbonitrile, 2-furonitrile and other nitriles which each have a sulphur atom or an oxygen atom as a heteroatom; 2-cyanopyridine, 3-cyanopyridine, 4-cyanopyridine, cyanopyrazine and other nitriles which each contain a nitrogen atom as a heteroatom; 5-cyanoindole and other fused heterocycles; cyanopiperidine, cyanopiperazine and other hydrogenated heterocyclic nitriles and fused heterocyclic nitriles.

The particularly preferred carbonitriles include especially α-hydroxycarbonitriles (cyanohydrins), for example hydroxyacetonitrile, 2-hydroxy-4-methylthiobutyronitrile, α-hydroxy-γ-methylthiobutyronitrile (4-methylthio-2-hydroxybutyronitrile), 2-hydroxypropionitrile (lactonitrile) and 2-hydroxy-2-methylpropio-nitrile (acetone cyanohydrin), particular preference being given to acetone cyanohydrin.

Surprising advantages can be achieved if the reaction mixture added to the manganese dioxide-comprising catalyst has a pH in the range from 6.0 to 11.0, preferably 6.5 to 10.0 and most preferably 8.5 to 9.5. In this connection, the pH is defined as the negative decadic logarithm of the activity of the oxonium ions ($H_3O^+$). This parameter thus depends upon factors including the temperature, this parameter being based on the reaction temperature. For the purposes of the invention, it is in many cases sufficient to determine this parameter with electrical measuring equipment (pH meters), a determination at room temperature being sufficient for many purposes instead of reaction temperature.

Without addition of an acid or base, a mixture of the reactants customarily used generally has a pH in the range from 3 to 5.5. Preference is therefore given to adding a basic substance to adjust the pH of the reaction mixture. To this end, it is possible with preference to use hydroxides or oxides, which are more preferably formed by alkaline earth metals or alkali metals. These include $Ca(OH)_2$ and $Mg(OH)_2$, MgO, CaO, NaOH, KOH, LiOH or $Li_2O$. Very particular preference is given here to using LiOH or $Li_2O$. It is theoretically also possible to use amines to adjust the pH. However, it has been found that the use of amines can have an adverse effect on the lifetime of the catalyst. The proportion of amines, especially to adjust the pH in the reaction mixture, is therefore preferably at most 0.1% by weight, more preferably at most 0.01% by weight and most preferably at most 0.001% by weight. In a particular aspect, no significant content of amine is added to adjust the pH of the reaction mixture. In the context of the present invention, ammonia ($NH_3$) is included among the amines.

In this context, it should be emphasized that the manganese dioxide-containing catalyst in many cases has amphoteric properties; the pH of the reaction mixture in the course of the reaction is therefore influenced significantly by the type and amount of the catalyst. The expression "the reaction mixture added to the manganese dioxide-comprising catalyst" makes it clear that the pH is measured without the presence of the catalyst. The further constituents of the reaction mixture include, for example, solvent, water, carbonitrile, etc.

It has been found that, surprisingly, hydrolysis in the presence of lithium ions leads to a particularly long lifetime of the manganese dioxide-comprising catalyst. To further improve the process according to the invention, it is accordingly possible to add lithium compounds, especially water-soluble lithium salts, to the reaction mixture, for example LiCl, LiBr, $Li_2SO_4$, LiOH and/or $Li_2O$. The concentration of lithium compounds is preferably in the range from 0.001 to 5% by weight, more preferably 0.01% by weight to 1% by weight. The addition can be effected during or before the hydrolysis reaction.

The hydrolysis of the carbonitrile to the carboxamide preferably takes place in the presence of an oxidizing agent. Suitable oxidizing agents are widely known in the technical field. These oxidizing agents include oxygen-containing gases; peroxides, for example hydrogen peroxide ($H_2O_2$), sodium peroxide, potassium peroxide, magnesium peroxide, calcium peroxide, barium peroxide, benzoyl peroxide and diacetyl peroxide; peracids or salts of peracids, for example performic acid, peracetic acid, sodium persulphate, ammonium persulphate and potassium persulphate; and oxo acids or salts of oxo acids, for example periodic acid, potassium periodate, sodium periodate, perchloric acid, potassium perchlorate, sodium perchlorate, potassium chlorate, sodium chlorate, potassium bromate, sodium iodate, iodic acid, sodium hypochlorite, permanganate salts, for example potassium permanganate, sodium permanganate and lithium permanganate, and salts of chromic acid, for example potassium chromate, sodium chromate and ammonium chromate.

The amount of the oxidizing agent used may be within a wide range, though the reactants and products should not be oxidized by the oxidizing agent. The oxidation sensitivity of these substances may therefore limit the use of the oxidizing agents. The lower limit arises from the improvement in the service life of the catalyst to be achieved. The molar ratio of oxidizing agent to carbonitrile is preferably in the range from 0.001:1 to 2:1, more preferably from 0.01:1 to 1.5:1.

These oxidizing agents can be added to the reaction mixture, for example, as a solution and/or as a gas. The oxidizing agents used are more preferably gases which comprise oxygen. In this case, the gas may comprise molecular oxygen ($O_2$) or ozone ($O_3$). In addition, the gas used as the oxidizing agent may comprise further gases, especially inert gases, such as nitrogen or noble gases. In a particular aspect, the gas may preferably comprise 50 to 98% by volume of inert gas and 2 to 50% by volume of molecular oxygen ($O_2$). The preferred gases include especially air. In addition, it is also possible to use a gas which contains less than 20% by volume, especially less than 10% by volume, of molecular oxygen, these gases comprising generally at least 1% by volume, preferably at least 2% by volume, of oxygen.

The amount of oxygen-comprising gas passed through the reaction mixture may preferably be in the range from 1 to 5000 and more preferably in the range from 10 to 1000 liters/hour, based on 1 kg of manganese dioxide-comprising catalyst.

The water which is needed to hydrolyse the carbonitrile can in many cases be used as the solvent. The molar ratio of water to carbonitrile is preferably at least 1; the molar ratio of water to carbonitrile is more preferably in the range of 0.5:1-25:1 and most preferably in the range of 1:1-10:1.

The water used for the hydrolysis may have a high purity. However, this property is not obligatory. In addition to fresh water, it is thus also possible to use tap water or process water which comprises greater or lesser amounts of impurities. Accordingly, it is also possible to use recycled water for the hydrolysis.

In addition, further constituents may be present in the reaction mixture for hydrolysis of the carbonitrile. These include carbonyl compounds such as aldehydes and ketones, especially those which have been used to prepare cyanohydrins for use with preference as the carbonitrile. For example, acetone and/or acetaldehyde may be present in the reaction mixture. This is described, for example, in U.S. Pat. No. 4,018,829-A. The purity of the aldehydes and/or ketones added is generally not particularly critical. Accordingly, these substances may comprise impurities, especially alcohols, for example methanol, water and/or methyl α-hydroxyisobutyrate (MHIB). The amount of carbonyl compounds, especially acetone and/or acetaldehyde, in the reaction mixture may be varied within wide ranges. The carbonyl compound is preferably used in an amount in the range of 0.1-6 mol, preferably 0.1-2 mol, per mole of carbonitrile.

The temperature at which the hydrolysis reaction is effected may generally be in the range of 10-150° C., preferably in the range of 20-100° C. and more preferably in the range of 30-80° C.

According to the reaction temperature, the hydrolysis reaction may be carried out under reduced or elevated pressure. This reaction is preferably carried out within a pressure range of 0.1-10 bar, more preferably 0.5 to 5 bar.

The reaction time of the hydrolysis reaction depends upon factors including the carbonitriles used, the activity of the catalyst and the reaction temperature, and this parameter may be within wide ranges. The reaction time of the hydrolysis reaction is preferably in the range from 30 seconds to 15 hours, more preferably from 15 minutes to 10 hours and most preferably 60 minutes to 5 hours.

In continuous processes, the residence time is preferably 30 seconds to 15 hours, more preferably 15 minutes to 10 hours and most preferably 60 minutes to 5 hours.

The loading of the catalyst with carbonitrile may be within a wide range. Preference is given to using 0.01 to 2.0, more preferably 0.05 to 1.0 and most preferably 0.1 to 0.4 g of carbonitrile per g of catalyst per hour.

The reaction can, for example, be carried out in a fixed bed reactor or in a suspension reactor. If gases are used as oxidizing agents, it is possible in particular to use so-called trickle bed reactors which enable good contact of gas, solid and liquid. In trickle bed reactors, the catalyst is arranged in the form of a fixed bed. The trickle bed reactor can be operated in cocurrent or countercurrent mode.

The reaction mixture thus obtained may generally, in addition to the desired carboxamide, comprise further constituents, especially unconverted carbonitrile and any acetone and/or acetaldehyde used. Accordingly, the reaction mixture can be purified, in which case, for example, unconverted cyanohydrin can be split into acetone and hydrogen cyanide, in order to use them again to prepare the cyanohydrin. The same applies to the acetone and/or acetaldehyde removed.

In addition, the reaction mixture comprising purified carboxamide can be freed of further constituents by means of ion exchange columns.

To this end, it is possible in particular to use cation exchangers and anion exchangers. Ion exchangers suitable for this purpose are known per se. For example, suitable cation exchangers can be obtained by sulphonating styrene-divinylbenzene copolymers. Basic anion exchangers in many cases comprise quaternary ammonium groups which are bonded covalently to styrene-divinylbenzene copolymers.

The purification of α-hydroxycarboxamides is described in more detail, inter alia, in EP-A-0686623.

The carbonitrile used for the hydrolysis can be obtained in any way. In the process according to the invention, the purity of the carbonitrile, for example of the cyanohydrin, is generally uncritical. Accordingly, it is possible to use purified or unpurified carbonitrile for the hydrolysis reaction.

To prepare cyanohydrins for use with preference, it is possible, for example, to react a ketone, especially acetone, or an aldehyde, for example acetaldehyde, propanal, butanal, with hydrogen cyanide to give the corresponding cyanohydrin. Particular preference is given here to reacting acetone and/or acetaldehyde in a typical manner using a small amount of alkali or of an amine as a catalyst. The amines used for the catalysis of this reaction can preferably be used in the form of basic ion exchange resins.

Accordingly, the carbonitrile can preferably be obtained by reacting a ketone or aldehyde with hydrogen cyanide in the presence of a basic catalyst. In a particular embodiment, the basic catalyst used may be an alkali metal hydroxide, in which case the amount of basic catalyst is preferably selected such that the pH of the mixture used for the hydrolysis reaction is adjusted to a value in the range from 6.0 to 11.0, preferably 6.5 to 10.0 and most preferably 8.5 to 9.5.

The hydrolysis reaction of the present invention may especially serve as an intermediate step in processes for preparing (meth)acrylic acids, especially acrylic acid (propenoic acid) and methacrylic acid (2-methylpropenoic acid), and alkyl (meth)acrylates. Accordingly, the present invention also provides a process for preparing methyl methacrylate which comprises a hydrolysis step by a process of the present invention. Processes which may comprise a hydrolysis step of cyanohydrins to prepare (meth)acrylic acid and/or alkyl (meth)acrylates are detailed, inter alia, in EP-A-0 406 676, EP-A-0 407 811, EP-A-0 686 623 and EP-A-0 941 984.

The present invention will be illustrated in detail hereinafter with reference to examples.

EXAMPLE 1

1123.0 g of manganese oxide (MnO2, HSA type, 1242239 type, commercially available from Erachem Comilog), 19.0 g of plasticizer A (Actigel 208, commercially available from ITC Minerals & Chemicals) and 19.0 g of plasticizer B (Arginotex NX Nanopowder, commercially available from B+M Nottenkämper, Gesellschaft für Bergbau and Mineralstoffe mbH u. Co. KG) are intensively dry-mixed in a mixer (Eirich, R 02 type) at an agitator speed of 1500 $min^{-1}$ and a plate speed of 84 $min^{-1}$ over two minutes.

Subsequently, with continued mixing, 445.1 g of aqueous silica sol solution (Koestrosol 0830 A, commercially available from Chemiewerk Bad Köstritz GmbH), containing 29% $SiO_2$, and 186.7 g of dist. water are added to this mixture which is mixed further until the agglomerates have reached a mean size of diameter 1-3 mm.

The moist pellets were dried at 100° C. over 10 h.

This affords approx. 1100 g of shaped catalyst bodies. The composition:

| | | |
|---|---|---|
| Manganese dioxide: | 87% | |
| Plasticizer A: | 1.5% | |
| Plasticizer B: | 1.5% | |
| Aqueous silica sol solution: | 10% | |
| | (calculated as $SiO_2$) | |

The theoretical composition of the pellets is shown in Table 1.

TABLE 1

Composition of the catalyst obtained in Example 1

| Constituent | | Content |
|---|---|---|
| $MnO_2$ | (%) | 81.196 |
| $SiO_2$ | (%) | 12.635 |
| $Fe_2O_3$ | (%) | 0.160 |
| $Al_2O_3$ | (%) | 0.457 |
| CaO | (%) | 0.122 |
| MgO | (%) | 0.183 |
| $Na_2O$ | (%) | 0.012 |
| $K_2O$ | (%) | 2.753 |
| $TiO_2$ | (%) | 0.019 |
| $P_2O_5$ | (%) | 0.005 |
| S | (%) | 0.073 |
| Ignition loss | (%) | 2.385 |
| Total | (%) | 100.000 |

To determine the mechanical properties of the catalyst, the specific side crushing strength was measured. In the measurement of the specific side crushing strength, a specimen is placed above a fixed pressing jaw and pressed with a mobile pressing jaw with increasing force until the specimen fractures. The fracture is detected electronically and the force expended until the time of fracture is reported. A constant rise in force of 50 N/s was employed here. The measurement was carried out with a TBH 250 measuring instrument from Erweka GmbH, D-63150 Heusenstamm. Further properties of the pellets obtained in Example 1 are shown in Table 2.

EXAMPLE 2

Example 1 was essentially repeated, except that the moist agglomerates were not dried, but rather processed in a Hutt granule shaping machine system (GR 1 type) to give extrudates with a diameter of 1.6 mm. The shaped catalyst was dried at 100° C. for 10 h.

To determine the mechanical properties of the catalyst, the specific side crushing strength was measured. Further properties of the extrudate obtained in Example 2 are shown in Table 2.

EXAMPLE 3

Example 1 was essentially repeated, except that the moist agglomerates were not dried but rather processed in a Schlüter annular die press system (PP127 type) to give extrudates with a diameter of 1.4 mm. The shaped catalyst was dried at 100° C. for 10 h.

To determine the mechanical properties of the catalyst, the specific side crushing strength was measured. Further properties of the extrudate obtained in Example 3 are shown in Table 2.

TABLE 2

Properties of the catalysts obtained in Examples 1 to 3

| Example | | 1 | 2 | 3 |
|---|---|---|---|---|
| Form | | Pellet | Extrudate | Extrudate |
| Diameter | mm | 1.5-2 | 1.6 | 1.4 |
| Length | mm | | 2-7 | 2-7 |
| Spec. side crushing strength | N/mm | 0.55 | 6.2 | 7.4 |

EXAMPLE 4

1000.0 g of manganese oxide (MnO2, HSA type, 1242239 type, commercially available from Erachem Comilog), 62.5 g of plasticizer (Actigel 208, commercially available from ITC Minerals & Chemicals) and 62.5 g of pulverulent binder (Sipernat 320r type, commercially available from Evonik Degussa GmbH) are dry-mixed intensively in a mixer (Eirich, R 02 type) at an agitator speed of 1500 min$^{-1}$ and a plate speed of 84 min$^{-1}$ over 2 minutes.

Subsequently, with continued mixing, 431.0 g of aqueous silica sol solution (Koestrosol 0830 A, commercially available from Chemiewerk Bad Köstritz GmbH), containing 29% $SiO_2$, and 230.0 g of dist. water are added to this mixture which is mixed further until the agglomerates have reached a mean size of diameter 1-3 mm.

The moist pellets were dried at 100° C. over 10 h.

This affords approx. 1200 g of shaped catalyst bodies. The composition:

| | |
|---|---|
| Manganese dioxide: | 80% |
| Plasticizer: | 5% |
| Pulverulent binder: | 5% |
| Aqueous silica sol solution: | 10% |
| | (calculated as $SiO_2$) |

The theoretical composition of the pellets is shown in Table 3.

To determine the mechanical properties of the catalyst, the BCS value (bulk crushing strength) was measured. To determine the BCS value, a small cylinder is filled with shaped bodies and subjected to increasing pressure from above with a plunger, always for a period of three minutes, until the resulting fracture (<=0.42 mm) has a proportion of 0.5% of the total amount of material used. The pressure corresponding to this proportion is reported in megapascal as the "BCS" value. The method is sufficiently well known as the "shell test" and is used principally for refinery catalysts.

The results obtained from the pellets obtained in Example 4 are shown in Table 4.

TABLE 3

Composition of the catalyst obtained in Example 4

| Constituent | | Content |
|---|---|---|
| $MnO_2$ | (%) | 74.284 |
| $SiO_2$ | (%) | 18.434 |
| $Fe_2O_3$ | (%) | 0.173 |
| $Al_2O_3$ | (%) | 0.495 |
| CaO | (%) | 0.099 |
| MgO | (%) | 0.461 |
| $Na_2O$ | (%) | 0.031 |
| $K_2O$ | (%) | 2.466 |
| $TiO_2$ | (%) | 0.022 |
| $P_2O_5$ | (%) | 0.000 |
| S | (%) | 0.067 |
| Ignition loss | (%) | 3.469 |
| Total | (%) | 100.000 |

EXAMPLE 5

Example 4 was essentially repeated, except that the moist agglomerates were not dried, but rather processed in a Hutt granule shaping machine system (GR 1 type) to give extrudates with a diameter of 1.6 mm. The shaped catalyst was dried at 100° C. for 10 h.

To determine the mechanical properties of the catalyst, the BCS value (bulk crushing strength) was measured. The results obtained from the extrudate obtained in Example 5 are shown in Table 4.

EXAMPLE 6

Example 4 was essentially repeated, except that the moist agglomerates were not dried, but rather processed in a Schlüter annular die press system (PP127 type) to give extrudates having a diameter of 1.0 mm. The shaped catalyst was dried at 100° C. for 10 h.

To determine the mechanical properties of the catalyst, the BCS value (bulk crushing strength) was measured. The results obtained from the extrudate obtained in Example 6 are shown in Table 4.

TABLE 4

Properties of the catalysts obtained in Examples 4 to 6

| Example | | 4 | 5 | 6 |
|---|---|---|---|---|
| Form | | Pellet | Extrudate | Extrudate |
| Diameter | mm | 1.5-2 | 1.6 | 1 |
| Length | mm | | 2-7 | 2-7 |
| BCS | N/mm | 0.88 | 1.05 | 0.62 |

For the values shown in Table 4, however, it should be noted that large particles tend to higher values, since smaller particles reach the proportion of fragments predefined as the end value more rapidly. The extrudate according to Example 5 is therefore significantly more stable than the pellets according to Example 4.

EXAMPLE 7

1167.0 g of manganese oxide (MnO2, HSA type, 1242239 type, commercially available from Erachem Comilog) and 145.9 g of plasticizer (Arginotex NX Nanopowder, commercially available from B+M Nottenkämper, Gesellschaft für Bergbau and Mineralstoffe mbH u. Co. KG) are intensively dry-mixed in a mixer (Eirich, R 02 type) at an agitator speed of 1500 min$^{-1}$ and a plate speed of 84 min$^{-1}$ over 2 minutes.

Subsequently, with continued mixing, at an agitator speed of 450 rpm, 487.9 g of aqueous silica sol solution (Koestrosol 0830 A, commercially available from Chemiewerk Bad Köstritz GmbH), containing 29% $SiO_2$, and 343 g of dist. water are added to this mixture which is mixed further until a homogeneous composition is obtained.

The moist composition was processed with a Händle screw extruder (PZVM8b type) to give cloverleaf-shaped extrudates. The shaped catalyst was dried at 100° C. for 10 h.

The composition of the catalyst is found to be:

| | |
|---|---|
| Manganese dioxide: | 80% |
| Plasticizer: | 10% |
| Aqueous silica sol solution: | 10% |
| | (calculated as $SiO_2$) |

The theoretical composition of the dried catalyst is shown in Table 5.

TABLE 5

Composition of the catalyst obtained in Example 7

| Constituent | | Content |
|---|---|---|
| $MnO_2$ | (%) | 74.721 |
| $SiO_2$ | (%) | 15.412 |
| $Fe_2O_3$ | (%) | 0.738 |
| $Al_2O_3$ | (%) | 2.109 |
| CaO | (%) | 0.633 |
| MgO | (%) | 0.316 |
| $Na_2O$ | (%) | 0.016 |
| $K_2O$ | (%) | 3.026 |
| $TiO_2$ | (%) | 0.084 |
| $P_2O_5$ | (%) | 0.032 |
| S | (%) | 0.067 |
| Ignition loss | (%) | 2.846 |
| Total | (%) | 100.000 |

EXAMPLE 8

1167.0 g of manganese oxide (MnO2, HSA type, 1242239 type, commercially available from Erachem Comilog) and 145.9 g of plasticizer (Arginotex NX Nanopowder, commercially available from B+M Nottenkämper, Gesellschaft für Bergbau and Mineralstoffe mbH u. Co. KG) are intensively dry-mixed in a mixer (Eirich, R 02 type) at an agitator speed of 1500 min$^{-1}$ and a plate speed of 84 min$^{-1}$ over 2 minutes.

Subsequently, with continued mixing, 487.9 g of aqueous silica sol solution (Koestrosol 0830 A, commercially available from Chemiewerk Bad Köstritz GmbH), containing 29% $SiO_2$, and 137.5 g of dist. water are added to this mixture which is mixed further until a homogeneous composition is obtained.

The moist composition was processed with a Schlüter annular die press to give 0.8 mm cylindrical rods. The shaped catalyst was dried at 100° C. for 10 h.

The composition of the catalyst is found to be:

| Manganese dioxide: | 80% |
|---|---|
| Plasticizer: | 10% |
| Aqueous silica sol solution: | 10% |
| | (calculated as $SiO_2$) |

The theoretical composition for the dried catalyst is shown in Table 6.

TABLE 6

Composition of the catalyst obtained in Example 8

| Constituent | | Content |
|---|---|---|
| $MnO_2$ | (%) | 74.721 |
| $SiO_2$ | (%) | 15.412 |
| $Fe_2O_3$ | (%) | 0.738 |
| $Al_2O_3$ | (%) | 2.109 |
| CaO | (%) | 0.633 |
| MgO | (%) | 0.316 |
| $Na_2O$ | (%) | 0.016 |
| $K_2O$ | (%) | 3.026 |
| $TiO_2$ | (%) | 0.084 |
| $P_2O_5$ | (%) | 0.032 |
| S | (%) | 0.067 |
| Ignition loss | (%) | 2.846 |
| Total | (%) | 100.000 |

COMPARATIVE EXAMPLE 1

To 1123.0 g of manganese oxide (MnO2, HSA type, 1242239 type, commercially available from Erachem Comilog), with continued mixing in a mixer (Eirich, R 02 type) at an agitator speed of 1500 min$^{-1}$ and a plate speed of 84 min$^{-1}$, are added 445.1 g of aqueous silica sol solution (Koestrosol 0830 A, commercially available from Chemiewerk Bad Köstritz GmbH), containing 29% $SiO_2$, and 186.7 g of dist. water, and mixing is continued until the agglomerates have reached a mean size of diameter 1-3 mm.

Attempts were made to process the moist agglomerates with a Händle screw extruder (PZVM8b type) to give cloverleaf-shaped extrudates. The extrusion begins with already very inhomogeneous extrudate emergence from the die plate. The material discharge becomes increasingly worse in terms of shape, and the pressure in the head upstream of the die plate, which begins at approx. 14 bar, rises rapidly to more than 30 bar. The increasingly worse extrudate emergence is accompanied by cessation of discharge for the most part. The machine is switched off at this time in order to prevent damage as a result of overloading. After the machine has been opened, the material in the pressure head upstream of the die plate has solidified.

EXAMPLES 9 TO 11

Example 7 was essentially repeated, except that the proportions by weight of the plasticizer and of the binder were altered. The moist aggregates were processed with a Händle screw extruder (PZVM8b type) to give extrudates of diameter 2 mm. The shaped catalyst was dried at 100° C. for 10 h. The specific side crushing strength of the resulting extrudates was studied. The results obtained are shown in Table 7.

TABLE 7

Strength of the catalysts obtained in Examples 9 to 11

| Example | Plasticizer w (%) | $SiO_2$ from sol w (%) | Strength (N/mm) |
|---|---|---|---|
| 9 | 5 | 5 | 5.9 |
| 10 | 5 | 10 | 8.8 |
| 11 | 5 | 15 | 9.4 |

In the range tested, the hardness increases with the binder content.

EXAMPLE 12

The properties of a catalyst obtained according to Example 1 were studied in a trickle bed reactor. To this end, a mixture of 30% by weight of acetone cyanohydrin, 40% by weight of water and 30% by weight of acetone was converted at a temperature of 60° C. and standard pressure. The loading of the catalyst was approx. 3 g of acetone cyanohydrin per g of catalyst per hour.

Additionally used were approx. 250 ml of air per minute at a pressure of approx. 1 bar, and the amount of catalyst was approx. 40 g.

The ACH conversion was 19.4%, the HIBA selectivity 95.4%.

EXAMPLE 13

Example 12 was essentially repeated, except that a catalyst obtainable according to Example 2 was used. The ACH conversion was 21%, the HIBA selectivity 97.5%.

EXAMPLE 14

Example 12 was essentially repeated, except that a catalyst obtainable according to Example 3 was used. The ACH conversion was 38.3%, the HIBA selectivity 97.0%.

EXAMPLE 15

Example 12 was essentially repeated, except that a catalyst obtainable according to Example 4 was used. The ACH conversion was 32%, the HIBA selectivity 74.1%.

EXAMPLE 16

Example 12 was essentially repeated, except that a catalyst obtainable according to Example 5 was used. The ACH conversion was 17%, the HIBA selectivity 97.0%.

EXAMPLE 17

Example 12 was essentially repeated, except that a catalyst obtainable according to Example 6 was used. The ACH conversion was 50.1%, the HIBA selectivity 96.1%.

These examples show that the inventive catalysts have outstanding properties. It is surprisingly possible through the shaping to improve the selectivity and the conversion.

The invention claimed is:

1. A catalyst comprising:
at least 60% by weight of manganese dioxide with an empirical formula $MnO_x$ where x is in the range from 1.7 to 2.0, and
a plasticizer,
wherein
in an X-ray spectrum (XRD) of the manganese dioxide the intensity of a reflection in the range from 32.0° to 42.0° is greater than the intensity of any other reflection in the range of from 20° to 65°,
a specific surface area of the manganese dioxide is from 100 to 1000 $m^2/g$,
the plasticizer is a clay mineral, and
the catalyst is dried at a temperature in a range from 10 to 200° C.

2. The catalyst according to claim 1, wherein the specific surface area is from 150 to 1000 $m^2/g$.

3. The catalyst according to claim 1, further comprising a binder.

4. The catalyst according to claim 3, wherein the binder comprises $SiO_2$.

5. The catalyst according to claim 3, wherein the binder is a silicate having a specific surface area in the range from 150 to 400 $m^2/g$.

6. The catalyst according to claim 3, wherein a total amount of plasticizer and binder is 1 to 30% by weight, based on the weight of the catalyst.

7. The catalyst according to claim 1, wherein a Moh's hardness of the plasticizer is from 0.5 to 3.

8. The catalyst according to claim 1, further comprising at least one of an alkali metal ion and an alkaline earth metal ion.

9. The catalyst according to claim 1, further comprising a promoter.

10. The catalyst according to claim 9, wherein the promoter is one selected from the group consisting of Ti, Zr, V, Nb, Ta, Cr, Mo, W, Zn, Ga, In, Ge, Sn and Pt.

11. The catalyst according to claim 1, wherein the weight % of the $MnO_x$ is at least 80%.

12. A process for preparing a catalyst according to claim 1, comprising mixing at least one pulverulent manganese dioxide and at least one pulverulent plasticizer to obtain agglomerates.

13. The process according to claim 12, wherein the mixture comprising at least one pulverulent manganese dioxide and at least one pulverulent plasticizer is admixed with a liquid binder.

14. The process according to claim 13, wherein the liquid binder comprises at least one silica sol.

15. The process according to claim 12, further comprising mixing a pulverulent binder.

16. The process according to claim 15, wherein the pulverulent binder is a framework silicate and/or a precipitated silica.

17. The process according to claim 12, wherein the agglomerates are obtained by a process comprising introducing energy in an intensive mixer.

18. The process according to claim 12, wherein the agglomerates obtained have a diameter in the range from 0.5 mm to 5 mm.

19. The process according to claim 12, wherein the agglomerates obtained are extruded.

20. A process for preparing a carboxamide comprising reacting a carbonitrile with water, wherein the reaction is carried out in the presence of a catalyst comprising manganese dioxide according to claim 1.

21. The process according to claim 20, wherein the reaction mixture added to the catalyst comprising manganese dioxide has a pH in the range from 6.0 to 11.0, and the hydrolysis is carried out in the presence of an oxidizing agent.

22. The process according to claim 20, wherein the carbonitrile is 2-hydroxy-2-methylpropio-nitrile or 2-hydroxypropionitrile.

23. The process according to claim 20, wherein the hydrolysis reaction is carried out in a trickle bed reactor.

24. The catalyst according to claim 1, wherein the catalyst is in the form of a dried extrudate having a bulk crushing strength (BCS) of at least 0.6 N/mm.

* * * * *